United States Patent [19]

Mercer, Jr. et al.

[11] 4,077,254

[45] Mar. 7, 1978

[54] IMPACT SIMULATION APPARATUS

[75] Inventors: Benjamin Mercer, Jr., Toledo, Ohio; Darius O. Riggs, Ottawa Lake, Mich.; Charles G. Vogel, Toledo, Ohio

[73] Assignee: Owens-Illinois, Inc., Toledo, Ohio

[21] Appl. No.: 790,503

[22] Filed: Apr. 25, 1977

[51] Int. Cl.² ............................................. G01N 3/08
[52] U.S. Cl. ..................................................... 73/94
[58] Field of Search ......................................... 73/94

[56] References Cited

U.S. PATENT DOCUMENTS

| | | | |
|---|---|---|---|
| 3,618,370 | 11/1971 | Dubble | 73/88 R |
| 3,702,563 | 11/1972 | Brady et al. | 73/12 |
| 3,831,437 | 1/1973 | Sheets | 73/94 |
| 3,885,421 | 5/1975 | Nakamura et al. | 73/94 |
| 3,991,608 | 11/1976 | McGuire et al. | 73/94 |

*Primary Examiner*—Charles A. Ruehl
*Attorney, Agent, or Firm*—D. T. Innis

[57] ABSTRACT

Apparatus for testing glass containers for structural defects which may occur in the sidewalls thereof and which may render the containers incapable of withstanding a normal handling through a filling line and packing where the containers will be subjected to abuse. The apparatus is particularly designed to handle non-round bottles or containers and essentially takes the form of a pair of vertically oriented, rotatable, bottle-engaging rollers which, upon engagement with opposite sides of the bottle, will move the bottle through the gap between the two rollers. One of the rollers is laterally movable and biased toward the other roller, which has its axis fixed. An adjustable pneumatic pillow having a controllable pressure is positioned to be used to bias the mounting for the movable roller. The movable roller and its mounting structure has limited movement about a vertical pivot that is non-coincident with the vertical axis of the roller. When a defective container is engaged by the two rollers, the container will be broken. By slight modifications of the drive system for rotating the two opposed rollers, the apparatus is adaptable for testing round containers and convex-concave flasks. The positioning of the rollers relative to a conveyor that brings the bottles to the area between the rollers is such that the bottles, when gripped between the two rotating rollers, are close to or adjacent the edge of the conveyor such that broken glass may fall from the conveyor into a cullet chute and not be carried on the top of the conveyor.

12 Claims, 7 Drawing Figures

IMPACT SIMULATION APPARATUS

BACKGROUND OF THE INVENTION

It has been the practice in the past to test glass containers whose particular intended service is for marketing of soft drinks and beer, where the product is under pressure, by inspecting these containers optically for checks, both in the finish and in the heel. It has also been suggested to check the sidewall of the container for variations in the thickness of the wall circumferentially about the container and at several selected vertical positions of the container. The presence of a check might result in a structural failure in the container when filled with a product under pressure. The sidewalls of the containers have, by and large, been inspected only by visual observation by selectors observing the containers as they move in succession past a diffuse light source. The selectors are capable of selecting out those containers which have gross defects and in some instances will be able to segregate containers having other, more obvious, defects such as checks, seeds and blisters. It has also been proposed in the past to check the structural strength of containers by subjecting them to an internal pressure test or, as is commonly known, a "bursting strength test." The "bursting strength test," however, normally is a test conducted on statistical samples of containers, and the samples are stressed by internal pressure to the point of failure. As would be expected, this type of test has not lent itself to being a high-speed production-type test where every container would be subjected to a specific internal pressure.

Applicants have found that by subjecting containers to a radial loading on the sidewall, that those containers which have structural defects in the walls thereof or have insufficient strength to withstand a specific load, will be broken and thus effectively selected out of a line of ware being produced. The external stressing of the container is found to be a fairly acceptable substitute for impact testing containers.

DESCRIPTION OF THE PRIOR ART

A number of patents have issued recently which describe glass container testing apparatus and methods which involve the application of a compressive force to the containers while in an upright position, with the compressive force being applied to opposite sides of the sidewalls thereof.

One patent, which is assigned to the assignees of the present invention, is McGuire et al, U.S. Pat. No. 3,991,608. In this patent, containers are moved along on the upper surface of the conveyor where they enter the space between a rotating wheel and a stationary pressure plate. The gap between the wheel and the pressure plate is such that the containers will be compressed as they are precessed through the gap by the rotation of the wheel. In this particular patent, the wheel is biased by a fluid motor in the direction of the pressure plate. Depending upon the force applied by the motor, the wheel will compressively load the container being tested. This loading is termed a "simulated impact test." A defective container will break.

Another patent, U.S. Pat. No. 3,702,563 issued Nov. 14, 1972, to Brady et al, discloses a somewhat similar apparatus to that described above with regard to McGuire et al. In this particular patent, a non-shiftable, rotating wheel precesses the bottles through a compression zone in which the pressure plate or shoe has the force applied to it. This is by way of distinction from the McGuire et al patent. The application of the force in Brady et al is achieved by the use of a pivoted lever system and an air cushion or pneumatic pillow.

Another patent, U.S. Pat. No. 3,885,421 issued May 27, 1975, to Nakamura et al, discloses a testing device in which a container again is moved and rotated by contact with a rotating wheel at one side and is contacted at the opposite side by a pressure plate or "pusher shoe." The handling equipment in this particular patent provides three starwheels, the first of which functions to segregate and separate the containers from each other and remove them from a moving conveyor in order to transfer the container to the second starwheel. The second starwheel then moves the containers through the compression testing area and thence to a third starwheel which will replace the container on the moving conveyor. The compressive force is applied in this patent by a fluid motor acting on the "pusher shoe." Other features which are not of particular significance with regard to the present application are also shown and described.

These three patents all have one thing in common and that is that they are fundamentally designed to test round containers, in view of the fact that in the operation of each of them, containers are held against a rotating wheel which will roll the container over a stationary shoe or plate.

A fourth patent, U.S. Pat. No. 3,831,437 issued Aug. 27, 1974, to Sheets, discloses an apparatus for testing containers that may be of a non-circular cross-section. In this patent, containers again are moved in a generally straight line while in an upright attitude and pass between a first rotating wheel and a second rotating wheel with the second wheel being biased toward the first rotating wheel. The containers are, therefore, squeezed as they pass between the two wheels. Generally speaking, the first wheel is mounted on a fixed axis, while the second wheel is rotatable about a generally vertical axis and has its inner periphery provided with a rolling, biasing system which, in effect, biases the inner rim of the second wheel in a radial direction toward the axis of the first wheel. It should be noted that the second wheel generally is supported in part by resilient means so that it yields as the container passes through the test zone. The patent teaches that the apparatus could be used to test both round and non-round containers.

SUMMARY OF THE INVENTION

This invention relates to apparatus for testing non-circular glass containers wherein the containers, moving in a generally straight line are diverted to the side of the conveyor, and are, at this point, compressed between two rotating rollers with one of the rollers having a stationary, vertical axis, with the second roller being mounted for rotation about a first vertical axis and also hinged movement about a second vertical axis and means for biasing the hingedly mounted roller in the direction of the other roller with a preselected force sufficient to break defective containers.

DETAILED DESCRIPTION OF THE DRAWINGS

Figure 1:
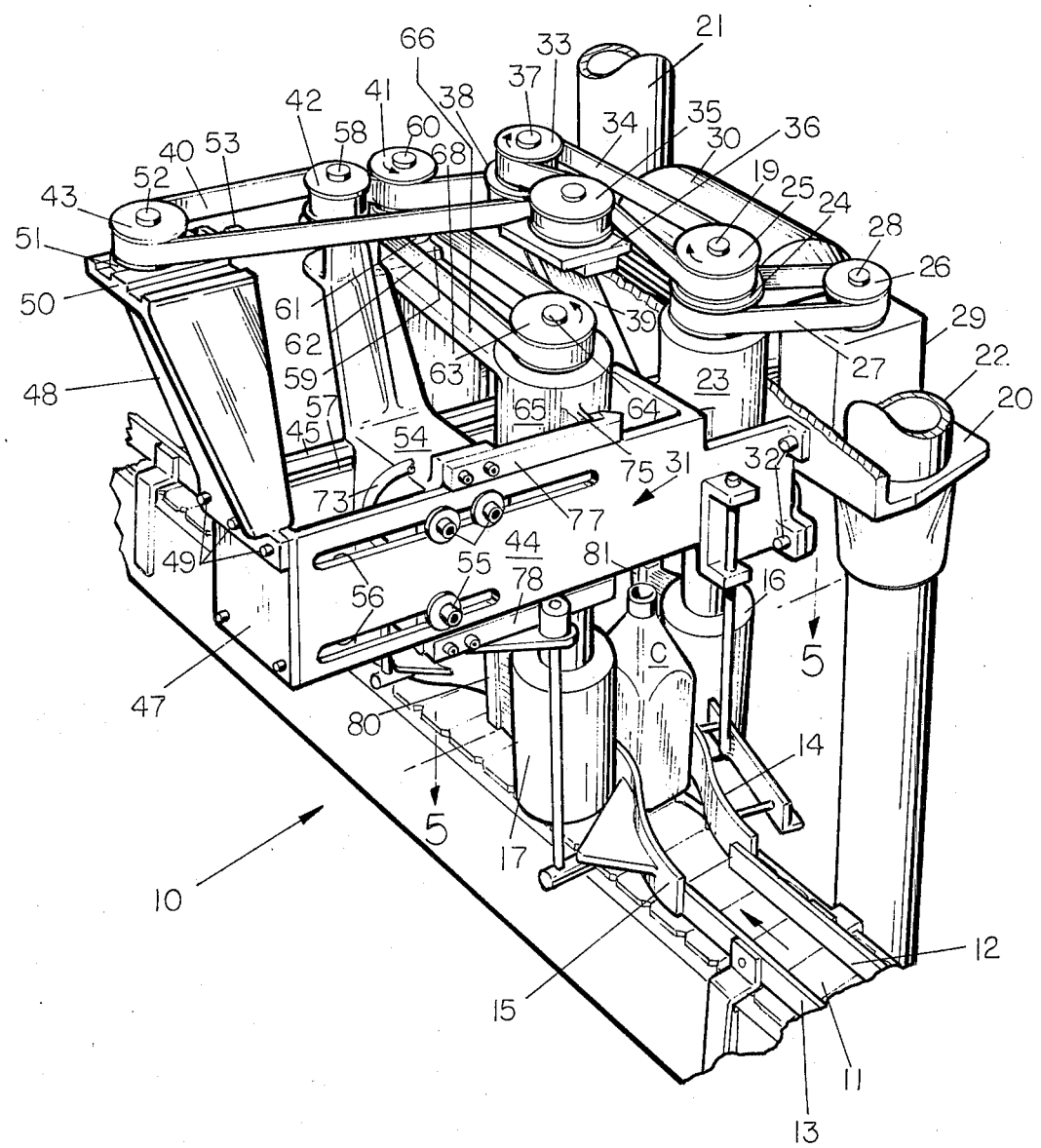
FIG. 1 is a perspective view of the container testing apparatus of the invention showing a container in testing position.
Figure 2:
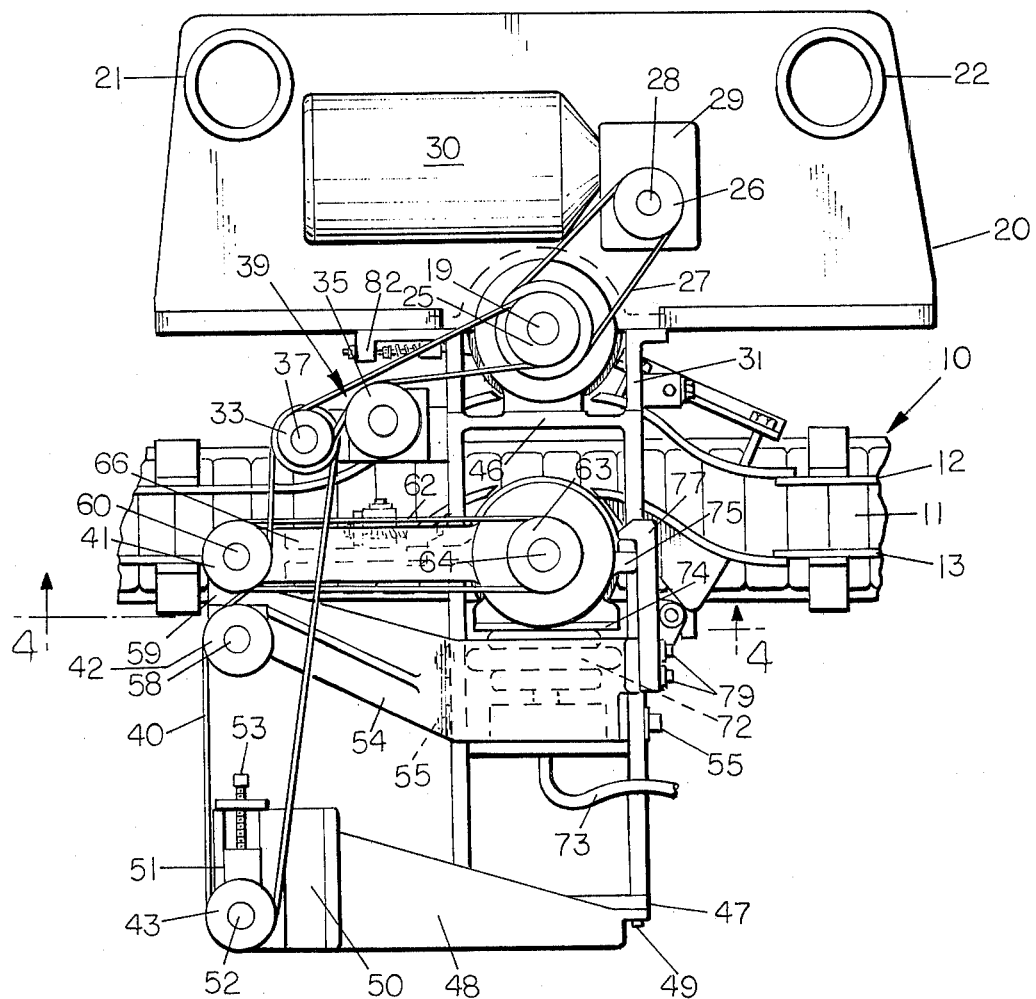
FIG. 2 is a top plan view of the apparatus of FIG. 1.

With particular reference to FIGS. 1 and 2, there is shown a generally horizontal conveyor 10 having an upper, articulated surface 11 which takes the form of an endless moving surface moving in the direction of the arrow indicated thereon in FIG. 1. A pair of stationary guide rails 12 and 13, spaced apart slightly more than the width of a container to be handled, extend over the surface 11 of the conveyor 10 at the incoming end thereof. A pair of curved guide rails 14 and 15 connect the exit end of the rails 12 and 13 and guide a container "C" to be tested to the testing zone or area which is located adjacent one side of the moving surface 11 of conveyor 10. The testing zone or area is defined by the space between a roller 16 and a roller 17. Both rollers 16 and 17 are provided with a resilient nylon or rubber-like facing 18 which can withstand glass penetration. The roller 16 is mounted on a shaft 19 which extends downwardly from an overhead supporting member 20. Supporting member 20, as best shown in FIGS. 1 and 2, is in the form of an angle bracket supported by a pair of hollow pillars 21 and 22.

The upper end of the shaft 19 passes through a support bearing housing 23 and carries a pulley 24 and a co-axially mounted pulley 25 thereon. The pulley 24 is rotationally connected to a drive pulley 26 by a belt 27. The drive pulley 26 is connected to an output shaft 28 of a gear box 29. The gear box 29 has its input drive shaft connected to an electric motor 30. Both the box 29 and the motor 30 are mounted on the upper surface of the supporting member 20. As a matter of fact, the bearing housing 23 is carried by the upper surface of a support casting 31. The casting 31 is bolted to the contoured, vertical face of the support member 20 by bolts 32.

With the above described mechanism, it can be seen that the roller 16 will be rotated by the operation of the motor 30. The pulley 25 is connected to a pulley 33 by a drive belt 34. A take-up pulley 35, mounted on a plate 36, is provided to keep tension on the belt 34. Pulley 33 is mounted on a shaft 37 and is coupled to a drive pulley 38 which is also mounted on the shaft 37. The shaft 37 and the plate 36 are both mounted to a support tower 39. The tower 39 is bolted to the side of the support casting 31 and extends upwardly and at an angle to the left, as viewed in FIGS. 3 and 4. The lower drive pulley 38 has a belt 40 in engagement therewith. The belt 40 is in driving engagement with pulleys 41, 42 and 43.

As can best be seen when viewing FIGS. 1 and 2, the support casting 31 takes the form of a generally rectangular enclosure formed of sidewalls 44 and 45, end wall 46 and the opposite end wall is formed by a plate 47. An arm 48 is bolted at its lower end at 49 to the plate 47 and, as can be best seen in FIG. 3, the arm 48 extends upwardly and to the left, and at its upper end forms a platform 50. The platform 50 supports a slideable block 51 within a horizontal groove formed in the upper platform surface. The block 51 supports a vertical stub shaft 52 which serves as the axle for the pulley 43. The block 51 may be adjusted by turning a screw 53. This adjustment is for the purpose of taking up any slack which may be in the belt 40.

Figure 4:
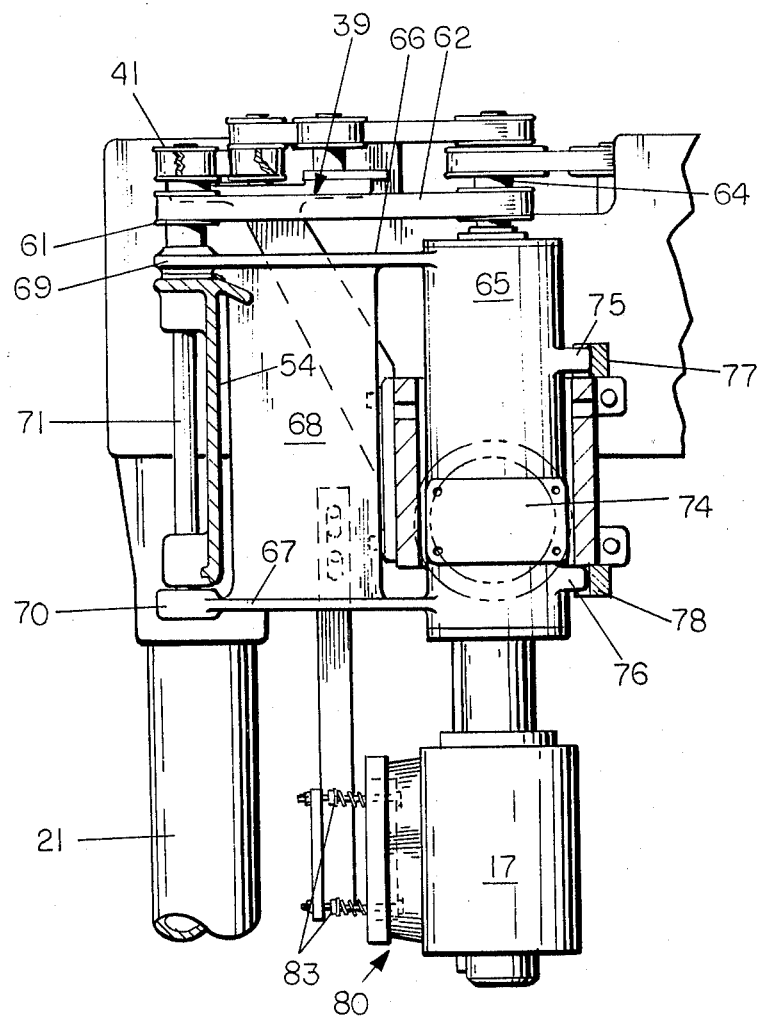
FIG. 4 is a cross-sectional view taken at line 4—4 of FIG. 2.

Intermediate the arm 48 and the tower 39 is a hinge forming support casting 54. This hinge support casting is mounted within the rectangular casting 31 by bolts 55 extending through horizontal slots 56 formed in the wall 44 of the support casting 31. Similar slots 57 are provided in the opposite wall 45. The casting 54 serves as the support for the pulley 42. A shaft 58 serves as the axle for the pulley 42, it being understood that the shaft 58 may be stationary with respect to the casting 54. The casting 54, at its upper, outwardly extending arm portion, carries the shaft 58 and on a lateral extension 59 of this upper end portion there is provided a vertical shaft 60. The shaft 60 rotatably supports both the pulley 41 and a pulley 61 located therebeneath. The pulley 61 is connected to rotate with the pulley 41 and is driven therewith such that when the belt 40 drives the pulley 41, the pulley 61 also will be driven which in turn will drive a belt 62 which is in engagement therewith. The belt 62 extends around a pulley 63. The pulley 63 is mounted on, and drives, a vertical shaft 64 that extends downward through a bearing supporting housing 65. The shaft 64 at its lower end drivingly supports the roller 17. The housing 65 is supported at the ends of a pair of horizontally extending arms 66 and 67. The two arms 66 and 67 are actually formed of a single casting connected together and reinforced by a web 68 and, as best shown in FIG. 4, the arms 66 and 67 at their ends remote from the housing 65 are formed with bearings 69 and 70. The bearings 69 and 70 provide a rotatable connection with a vertical hinge pin 71 carried by the hinge support casting 54.

Thus it can be seen that operation of the motor 30 will drive both the roller 16 and roller 17 in the directions indicated by the arrows on the tops thereof in FIG. 1. This is through the system of pulleys and belts described above.

The lower portion of the support casting 54, which is positioned between the sidewalls 44 and 45 of the casting 31, serves as the mounting member for a pneumatic pillow 72, similar to that shown in the above-referred-to Brady et al patent. The interior of the pillow is connected to a fluid pressure line 73 which may be connected to a suitable source of fluid under pressure with the gauges and valves necessary to provide an indication and control of the actual internal pressure within the pillow 72. One end of the pillow is seated within the casting 54 at the location of the pressure line 73 connection, while the other end of the pillow is connected to a plate 74 mounted on the side of the bearing housing 65. In this manner the bearing housing 65 and the roller 17 supported thereby are biased in the direction of the other, non-shiftable roller 16 by the pneumatic pillow 72.

As previously explained, the bearing housing 65 is hingedly mounted so that it may swivel about the hinge pin 71. To prevent over-travel of the housing 65 in the event a container is broken by the lateral force exerted between the two rollers 16 and 17, the housing 65 is provided with a pair of radially extending lugs 75 and 76. These lugs will engage stop fingers 77 and 78 which are mounted to the support casting 54 by bolts 79. The stop fingers, as it can readily be seen, will prevent the pneumatic pillow from becoming over-extended when the bearing housing moves with the roller 17 upon breakage of a container under test. It should be understood that the adjustment of the support casting 54 within the casting 31, for a particular size of bottle to be tested, will result in the bearing housing 65 being positioned so that the stop fingers 77 and 78 will not come into play when a container is being stressed unless breakage occurs. It is also understood that as a container passes between the rollers 16 and 17, the bearing housing 65 will move toward the pillow 72 and compress this pillow to a certain degree depending upon the pneumatic pressure within the pillow. When adjustment is made for ware of a larger size, the entire casting 54 may be moved toward the end plate 47 by loosening the bolts 55. This movement will result in the bearing housing 65, arms 62 and 67 with the casting 54 and pulleys 41, 42 and 61 moving as a unit. This adjustment does not disturb the tension or effective length of the belt 40 since the belt passes around one side of the pulley 41 and over the outside of the pulley 42. The pulley 43 will remain in its fixed position as does the pulley 38.

Figure 5:
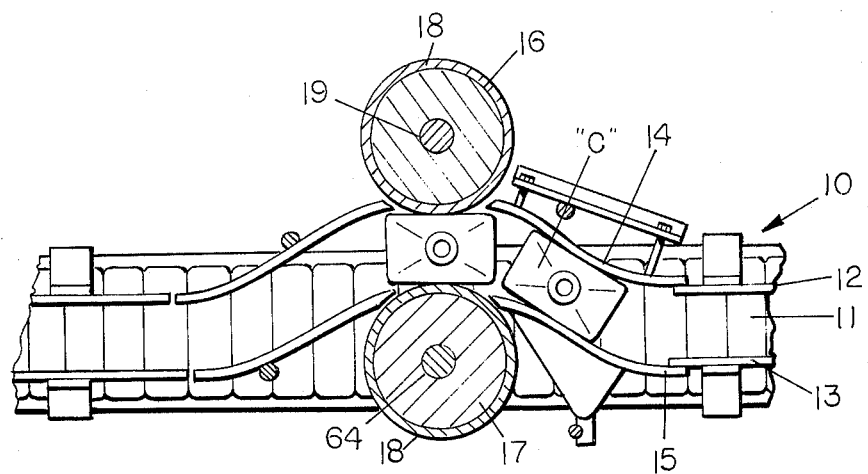
FIG. 5 is a cross-sectional plan view taken in the plane of 5—5 of FIG. 1.

It should also be pointed out that the side rails 12 and 13 at the incoming side have essentially their counterpart rails at the outgoing or exit of the testing apparatus, as shown in FIG. 5. In addition, curved guides are provided for directing the ware back to the center of the moving conveyor surface 11.

Figure 3:
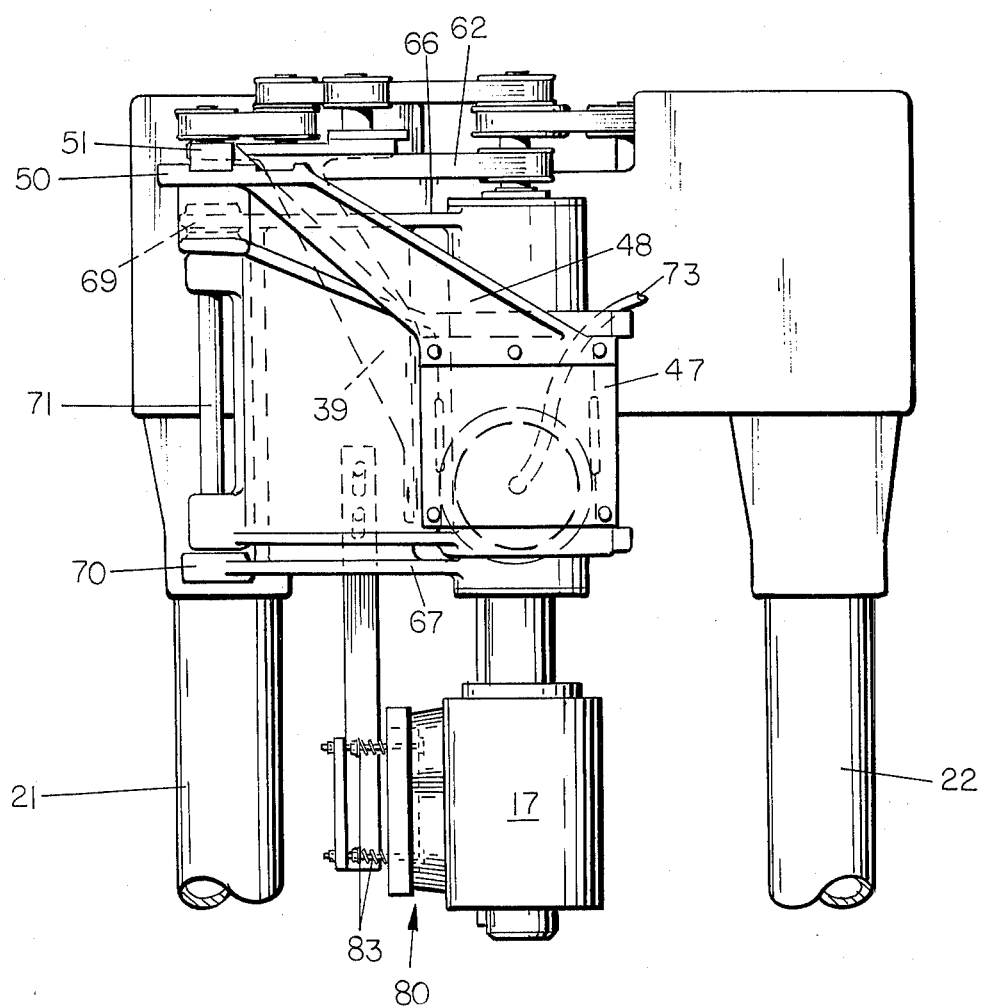
FIG. 3 is a front elevational view of the apparatus of FIG. 2.

As best shown in FIGS. 3 and 4, the roller 17, at the left-hand side thereof, has a cleaning brush 80 in engagement therewith, with the brush 80 being vertically adjustable to accommodate for positioning of the rollers 16 and 17 at differing heights depending upon the height of the container being inspected. The brush 80 serves to keep the rollers clean, it being recognized that upon failure of a container, bits of glass may statically cling to the roller surface. The brush 80 has its counterpart 81, partially shown in FIG. 1, in engagement with the roller 16. The brush 80 is mounted to the web 68 of the arms 66 and 67. The brush 81 is mounted to the support bracket 20 at 82. Inasmuch as the roller 16 is not adjustable relative to its support, the brush 81 also will not need to be moved when adjustments are made. Both the brushes are mounted to arms which extend downwardly and their lower ends are provided with openings through which horizontal pins that actually carry the brushes may extend, with springs taking up the tension and biasing the brushes in the direction of the rollers. The springs, as shown in FIGS. 3 and 4 at 83, assure that the brushes are biased against the rollers 17 and 16 and also will provide a certain amount of automatic adjustment or take-up relative to the anticipated wear of the brushes themselves.

The foregoing description of the apparatus clearly sets forth the function of the apparatus as a system for handling and testing containers for structural defects, in which the non-round containers are squeezed between two moving surfaces with a force that can be preselected. The apparatus is easily adjustable so that it may be used to test containers of various sizes and capacity without a major amount of realignment time being required. The apparatus will test containers of a wide variety of shapes, such as oblong, square, rectangular, etc., in cross-section.

Figure 6:
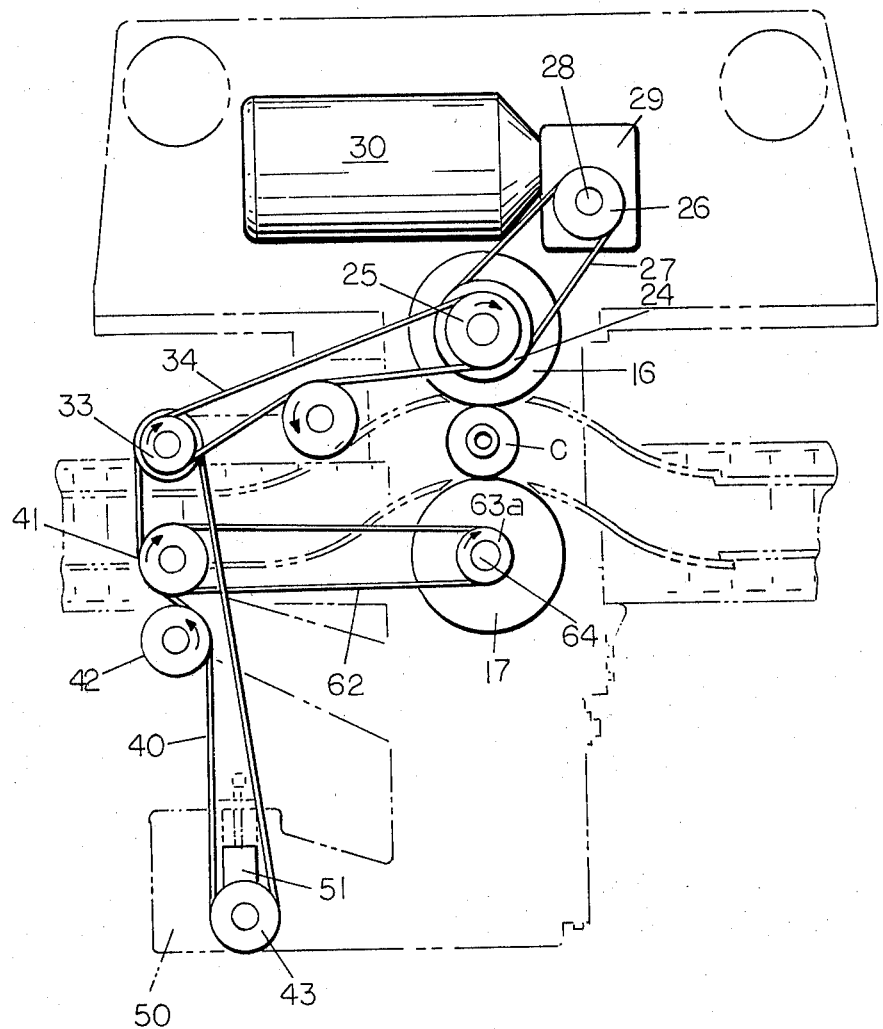
FIG. 6 is a schematic plan view, similar to FIG. 2, of modified apparatus for testing round containers.

Turning now to FIG. 6 a schematic plan view of the apparatus of FIG. 2 is shown, with a modification of the pulley and belt drive arrangement providing for the testing of containers that are round. In this modification, those elements which are identical to the mechanisms of FIGS. 1-5 will be provided with the same reference numerals. Only those new elements will have a new or different reference numeral.

The gear box 29 drives the pulley 26, belt 27 and roller 16. In this embodiment, the pulley 33 is driven by the belt 34. It should be noted that the pulley 33 has its axis moved to the left, as viewed in FIG. 6, from the position it previously occupied in FIG. 2. Pulley 33 and pulley 38 thereunder are shifted as a unit to the position shown in FIG. 6. Pulley 38, through belt 40, will drive the pulley 41 in the direction shown by the arrow thereon. It should also be noted that the pulley 43 and its mounting block 51 are also shifted to the right on the platform 50 into the other mounting slot provided. As can be seen, the belt 40 therebefore drives the pulley 41 in the direction opposite to the direction of drive previously described with respect to the pulley 41 of FIG. 2. In this manner the roller 17 will be driven in a clockwise direction, as shown by the arrow thereon. It should also be pointed out that a pulley 63a which is carried by the shaft 64 of roller 17 is made smaller than the previously described pulley 63, so that this pulley 63a, being somewhat smaller, will rotate the surface of the roller 17 at a slightly different velocity than the surface of the roller 16 is being rotated. In this manner a round container "C" will be rotated about its vertical axis between the rollers 16 and 17 through a portion of its circumference before the container precesses to the extent that it will move from between the two rollers. This permits the use of essentially the same overall apparatus for testing round containers without the necessity of extensive refitting or adjusting the mechanical members or using a backup plate such as that shown in the prior art in place of one of the rollers.

Figure 7:
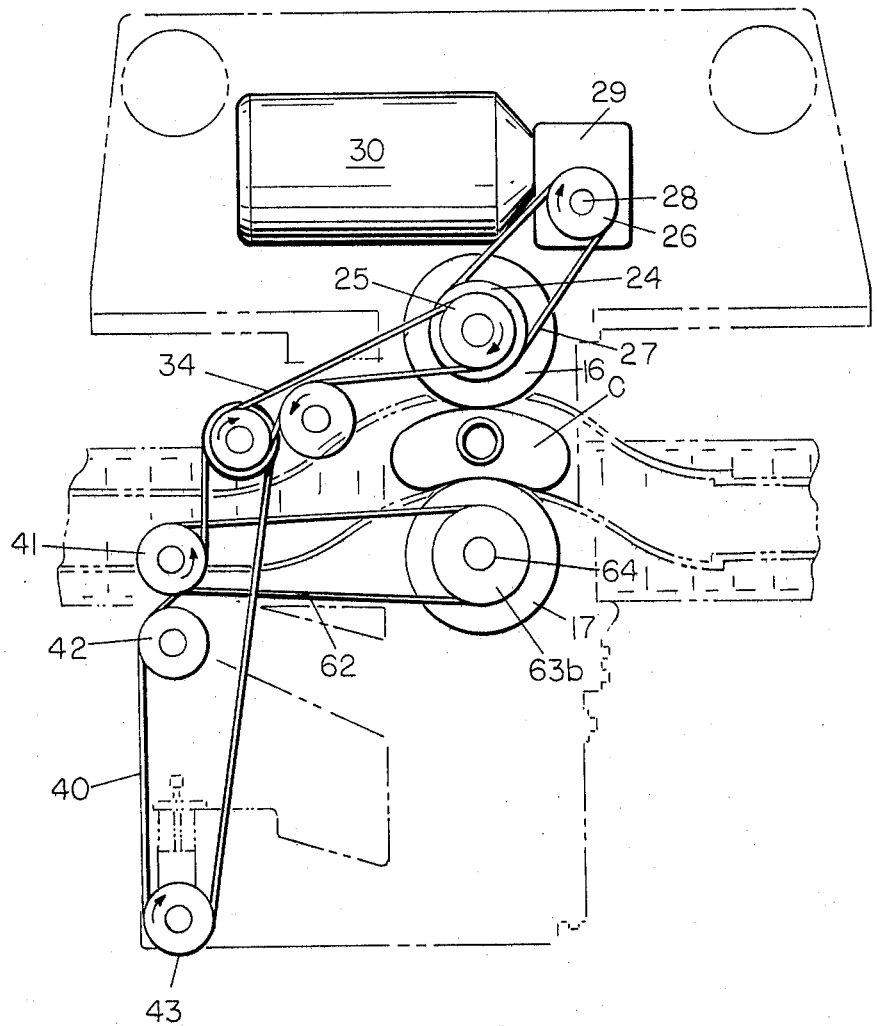
FIG. 7 is a schematic plan view, similar to FIG. 2, of modified apparatus for testing flasks.

Turning now to FIG. 7 the modification of the apparatus of FIGS. 1-5 will be described which permits the testing of flasks. As might be expected, if the apparatus of FIGS. 1-5 were to be used to test flasks which have somewhat parallel but curved surfaces, as shown in FIG. 7, there would be a tendency for the flask "C" to be thrown toward the top of FIG. 7 view. Due to the fact that the two opposed sides of the container, when in the shape of a flask are of different lengths, and to correct for this so as to enable the essentially same apparatus to function to test flasks, a pulley 63b is made larger than the previously described pulley 63 in the FIG. 2 embodiment. In this manner the periphery of the roller 17 will be moving slower than the periphery of the roller 16. Thus the flasks will pass through the gap between the two rollers and be stressed thereby without creating turning moments with regard to the central, vertical axis of the flask "C."

It should be noted that in FIG. 7, the drive belt and pulley arrangement of FIG. 2 remains intact and is not changed as was the case with respect to the embodiment of FIG. 6. This is because a reversal of drive direction of the roller 17 is not needed.

In view of the foregoing, it can be seen that the disclosed apparatus, while particularly suited for the testing of containers of the general shape shown in FIG. 1, the apparatus also, with slight modifications, is adapted to be used for the testing of round containers and flasks. Thus a universal container stressing test apparatus is provided by the disclosed invention.

We claim:

1. Apparatus for testing glass containers for structural defects, wherein the containers are transported on a moving conveyor with their axes generally vertical and guided along a predetermined path that diverges from the centerline of the conveyor to adjacent an edge thereof, the improvement characterized by:
  a pair of rotatable rollers;
  means for rotating said rollers;
  means mounting said rollers with their axes vertical adjacent said edge of the conveyor;
  means connected to one of said rollers for adjusting the relative spacing of said rollers;
  a vertical hinge;
  means mounting the adjustable roller for movement about said hinge; and
  means biasing said one roller in the direction of the other with a preselected force.

2. The apparatus of claim 1 wherein said biasing means comprises a pneumatic pillow.

3. The apparatus of claim 1 further including means connected to said movable roller mounting for limiting the movement thereof toward the stationary roller upon breakage of ware under test.

4. The apparatus of claim 1 further comprising a support for said hinge and means for adjusting said hinge and movable roller as a unit relative to said stationary roller.

5. The apparatus of claim 4 wherein said means for rotating said rollers comprises a shaft extending upward from said rollers and a pulley on each shaft and motor driven belt means interconnecting said pulleys.

6. The apparatus of claim 1 wherein said means for rotating said rollers is interconnected to rotate both rollers in opposite directions.

7. The apparatus of claim 6 wherein said means for rotating said rollers comprises pulley means on each roller and an interconnected belt drive system for said pulleys.

8. The apparatus of claim 7 wherein said pulleys are of the same diameter whereby said rollers will engage opposite sides of a non-circular, symmetrical container and stress the container without rotating the container about its vertical axis.

9. The apparatus of claim 7 wherein said pulleys are of somewhat different diameter whereby said rollers will engage opposite sides of a flask-style container having convex-concave sides and stress the flask without rotating the flask about its vertical centerline.

10. The apparatus of claim 1 wherein said means for rotating said rollers is interconnected to rotate both rollers in the same direction.

11. The apparatus of claim 10 wherein said means for rotating said rollers comprises pulley means on each roller and a belt drive system for said pulleys.

12. The apparatus of claim 11 wherein said pulleys are of different diameters whereby one roller is driven at a slightly higher angular velocity than the other to thereby provide rotation of a round container while being stressed.

* * * * *